United States Patent [19]
Wernicke et al.

[11] Patent Number: 5,571,150
[45] Date of Patent: Nov. 5, 1996

[54] TREATMENT OF PATIENTS IN COMA BY NERVE STIMULATION

[75] Inventors: Joachim F. Wernicke, League City; Reese S. Terry, Jr.; Ross G. Baker, Jr., both of Houston, all of Tex.

[73] Assignee: Cyberonics, Inc., Webster, Tex.

[21] Appl. No.: 358,264

[22] Filed: Dec. 19, 1994

[51] Int. Cl.⁶ .................................................. A61N 1/36
[52] U.S. Cl. ............................................................. 607/72
[58] Field of Search ................................. 607/44, 45, 68, 607/72

[56] References Cited

U.S. PATENT DOCUMENTS

| | | | |
|---|---|---|---|
| 3,522,811 | 8/1970 | Schwartz et al. | 607/44 |
| 3,918,461 | 11/1975 | Cooper | 607/45 |
| 4,702,254 | 10/1987 | Zabara | 607/45 |
| 4,873,981 | 10/1989 | Abrams et al. | 607/45 |

*Primary Examiner*—William E. Kamm
*Attorney, Agent, or Firm*—Wigman, Cohen, Leitner & Myers, P.C.

[57] ABSTRACT

A method of treating a patient in coma is performed by placing an electrode in juxtaposition with a preselected cranial nerve of the patient for electrical stimulation of the nerve, applying an electrical pulse waveform to the electrode to stimulate the cranial nerve, and adjusting electrical parameters of the pulse waveform to modulate electrical activity of the nerve in an effort to rouse the patient from the coma. The patient's response to the treatment is monitored and assessed by the attending physician according to Glasgow coma scale. The preferred cranial nerve is the vagus nerve, and the stimulation is performed either for acute treatment by positioning an esophageal electrode in the patient for stimulating a region of the vagus nerve in the neck, or for longer term treatment by implanting a nerve electrode on the vagus nerve. The electrical parameters of the pulse waveform to be adjusted, by programming, include pulse frequency, pulse width, pulse current, pulse voltage, waveform on time, and waveform off time. The programming is performed to control the patient's EEG activity by said modulation of the electrical activity of the vagus nerve. Preferably, the EEG activity is desynchronized.

19 Claims, 3 Drawing Sheets

TREATMENT OF PATIENTS IN COMA BY NERVE STIMULATION

BACKGROUND OF THE INVENTION

The present invention relates generally to methods and apparatus for treating or controlling medical, psychiatric or neurological disorders by application of modulating electrical signals to a selected nerve or nerve bundle of the patient, and more particularly to techniques for treating comatose patients by application of signals to a preselected cranial nerve, specifically the vagus nerve, using an implanted neurostimulating device.

Coma may be defined as a state of profound unconsciousness from which the patient cannot be roused by ordinary treatment. The name is derived from the Greek word koma, which means deep sleep, but in fact coma is not sleep at all, but a state of unconsciousness usually caused by injury or illness. In general, unlike patients who experience even very deep sleep such as in narcolepsy (sudden uncontrollable sleep attacks and cataplexy, often accompanied by visual or auditory hallucinations at the onset of sleep), the comatose patient displays no spontaneous eye movement, nor response to painful stimuli (in deep stages of coma), nor ability to speak. There are, however, degrees of conscious impairment in patients which may not rise to the level of coma, as measured by the Glasgow coma scale. Under that scale, in which best motor response, best verbal response, and minimum stimulus to cause eye opening are tested and scored, the scores may range from 3 to 15. A score of 3 indicates no motor response (regardless of cause), no vocalization even in response to noxious stimulus, and no eye opening in response to noxious stimuli. Scores of 7 or less on the Glasgow scale qualify as coma.

It will be appreciated that coma is not a single uniform disorder, but may stem from different causes such as trauma, disease, toxic condition or other condition, and which may be characterized by different levels of consciousness. It is a principal object of the present invention to provide new and improved methods for treating patients suffering degrees of conscious impairment constituting coma, regardless of cause of the coma.

SUMMARY OF THE INVENTION

The present invention provides a method for treating patients in coma, characterized by direct electrical stimulation of the vagus nerve (the tenth cranial nerve) with electrical impulses or waveforms designed to modulate the electrical activity of the nerve. The modulation is preferably selected to cause nerve afferents to conduct modified electrical patterns toward the reticular formation for desynchronizing the patient's EEG. In relatively few cases, it may be preferable to modulate the vagal activity to produce synchronization of the EEG. In either event, the technique involves modulating the activity of a number of brain structures, including the limbic system and the hippocampus, as well as the reticular formation.

Preferably, this vagal stimulation is carried out continuously while the patient is comatose, and is continued on a periodic basis after the level of motor, verbal and eye opening responses indicates that although the patient has been aroused from the coma, the degree of conscious impairment remains substantial. Alternatively, the treatment may be administered as a periodic or even random vagal stimulation. This would depend in part on whether a "carryover" or refractory period exists after stimulation in which the benefit of the stimulation continues. During the entire period of therapy, even those intervals where no stimulation is being performed, the patient's EEG is monitored to assess the state of synchronization or desynchronization of its activity and to detect changes of state.

The desired alteration of the EEG is achieved by appropriately adjusting, or programming, the electrical parameters of a pulse waveform applied to the vagus nerve to selectively modulate its electrical activity. It is postulated that such vagal stimulation will produce an improvement in the patient's responses and a return to at least partial consciousness.

In addition to monitoring the patient's EEG, the degree of conscious impairment of the patient is monitored by testing according to the Glasgow coma scale under the direction of the physician. Alternatively, the physician may apply techniques other than the Glasgow scale to assess the level of conscious impairment of the patient.

The therapy is applied using a neurostimulator having an output pulse waveform with parameters such as pulse width, amplitude (voltage or current), frequency, and signal on and off times which may be programmed directly or through telemetry by the attending physician. Preferably, for acute treatment, the output of an external signal (stimulus) generator of the neurostimulator is applied to the vagus nerve by means of a unipolar esophageal electrode which has been positioned for stimulation at a predetermined location of the nerve in the patient's neck. This avoids any need to invasively implant the neurostimulator or any portion of it into the body of the patient. Alternatively, or for the longer term where the patient does not respond to that form of acute treatment, the stimulus generator output is applied to the vagus nerve via an electrical lead having a bipolar electrode array implanted on the nerve at the neck site.

Where long term therapy is prescribed, the entire neurostimulator may be implemented in a battery operated package adapted to be fully implanted, along with the lead, into the patient. Changes in the programming may be carried out by telemetry. The implanted device lessens the need for relatively continual attention to an exit point of the lead to guard against infection if the stimulus generator portion were external to the patient.

Accordingly, a principal object of the present invention is to selectively modulate the electrical activity of a cranial nerve, especially the vagus nerve, to treat a comatose patient.

A related object is to modulate electrical activity of afferent nerve fibers to alleviate consciousness impairment by desynchronizing or synchronizing the patient's EEG.

BRIEF DESCRIPTION OF THE DRAWINGS

The above and still further objects, aspects, features and attendant advantages of the present invention will be better understood from a consideration of the following detailed description of the current best mode of practicing the invention, including a presently preferred embodiment and method thereof, taken in conjunction with the accompanying drawings, in which.

DESCRIPTION OF THE PRESENTLY PREFERRED EMBODIMENTS AND METHODS

Figure 1:
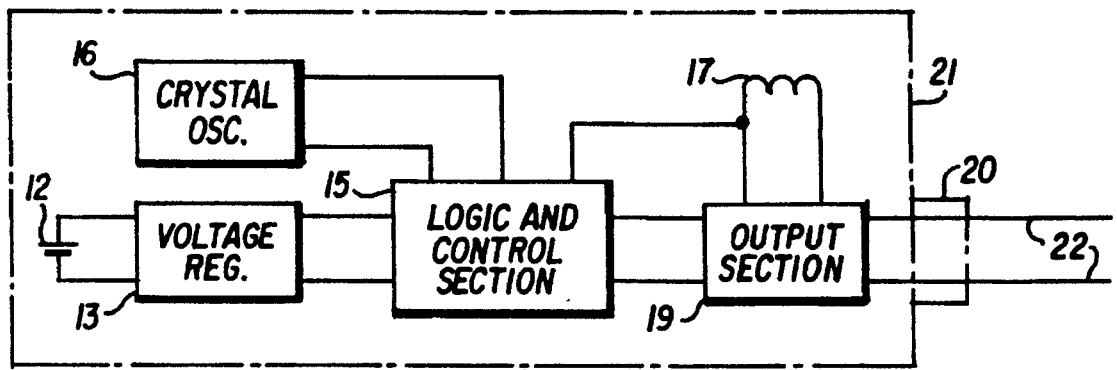
FIG. 1 is a simplified block diagram of a neurostimulator electronic stimulus generator for use in treating a comatose patient according to the invention.

A simplified block diagram of a suitable stimulus generator 10 of the neurostimulator adapted to be implanted in a patient is illustrated in FIG. 1. A suitable embodiment of the neurostimulator is described in detail in U.S. Pat. No. 5,154,172 of Reese S. Terry, Jr., et al. (referred to herein as "the '172 patent"), which is assigned to the same assignee as this application. The specification of the '172 patent is incorporated into this specification in its entirety, but some of the principal components of the neurostimulator will be described here for convenience.

The neurostimulator may include a conventional microprocessor and other electrical and electronic components. The stimulus generator 10 includes a battery 12, such as a lithium thionyl chloride cell, having terminals connected to a voltage regulator 13 which produces a clean, steady output voltage. Voltage multiplication or division may be used for a specific application. Regulator 13 supplies power to the electrical components of the generator, including logic and control section 15 for controlling, among other things, programmable functions of the device. The programmable functions relate to electrical parameters of the pulse waveform generated by the stimulus generator. The programmable parameters of particular interest include output current or voltage, output signal frequency, output signal pulse width, output signal on-time, output signal off-time, daily treatment time for continuous or periodic modulation of vagal activity, and output signal-start delay time.

Figure 2:
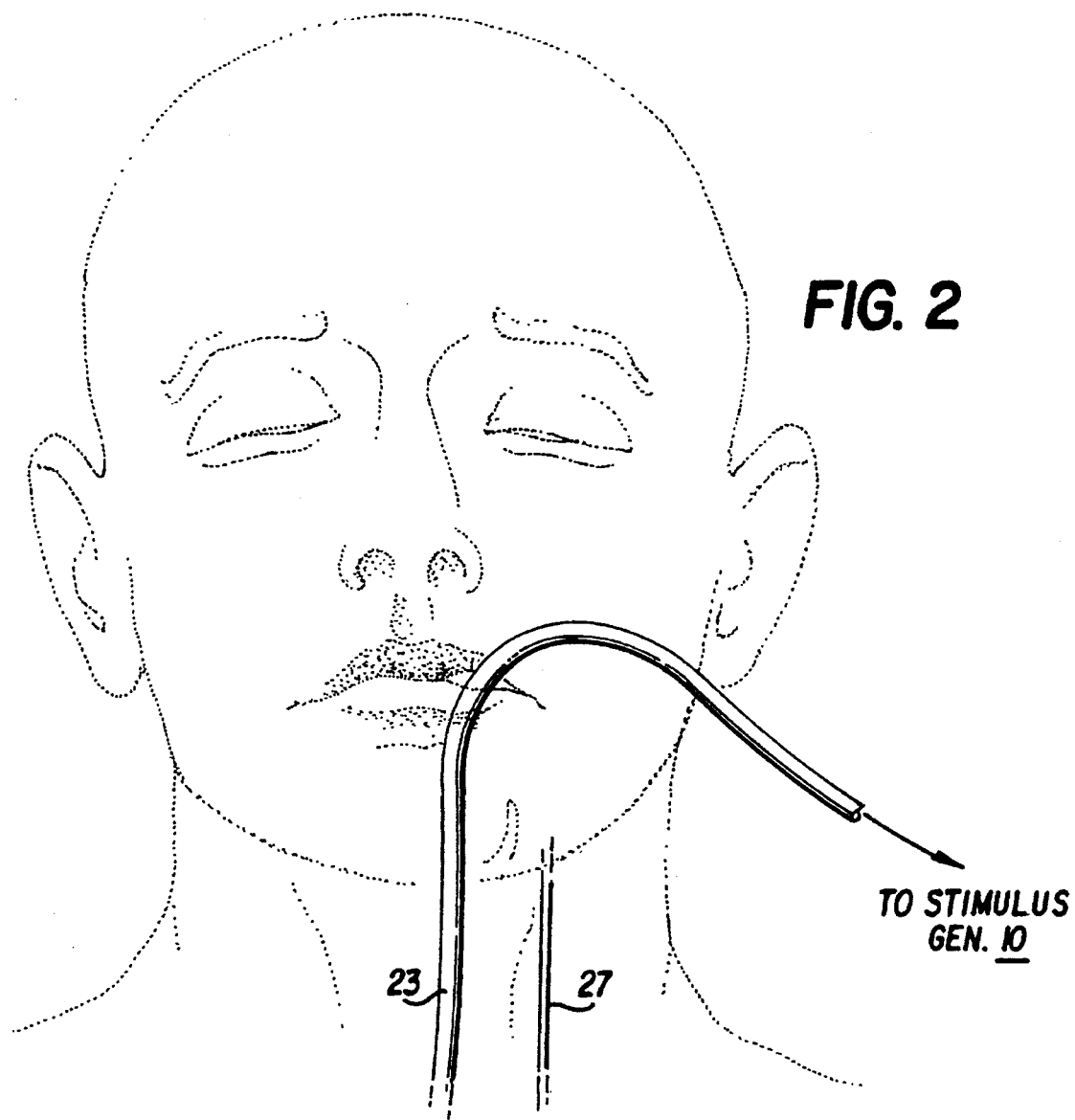
FIG. 2 is a simplified fragmentary illustration of the placement of an esophageal electrode energized by an external stimulus generator to treat the patient in coma.

Logic and control section 15 controls an output section 19 which generates the output pulse signal with programmed (prescribed) electrical parameters designated by the attending physician to treat the comatose patient. The output section is electrically coupled to receptacle terminals of electrical connector 20 which is mounted on the case 21 that houses the device. The proximal end of a lead 22 having a stimulating electrode at its distal end, is plugged into the connector receptacles. For acute treatment of the patient, the preferred electrode is a unipolar esophageal electrode 23 (FIG. 2) introduced into the comatose patient's throat and positioned to electrically stimulate the vagus nerve at a selected region in the neck when the electrode is energized by the output pulse waveform of the generator.

Figure 4:
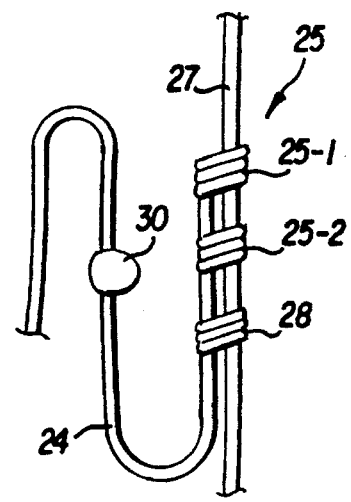
FIG. 4 is a detailed fragmentary illustration of the nerve electrode of FIG. 3 implanted on the vagal nerve in the neck of the patient.
Figure 3:
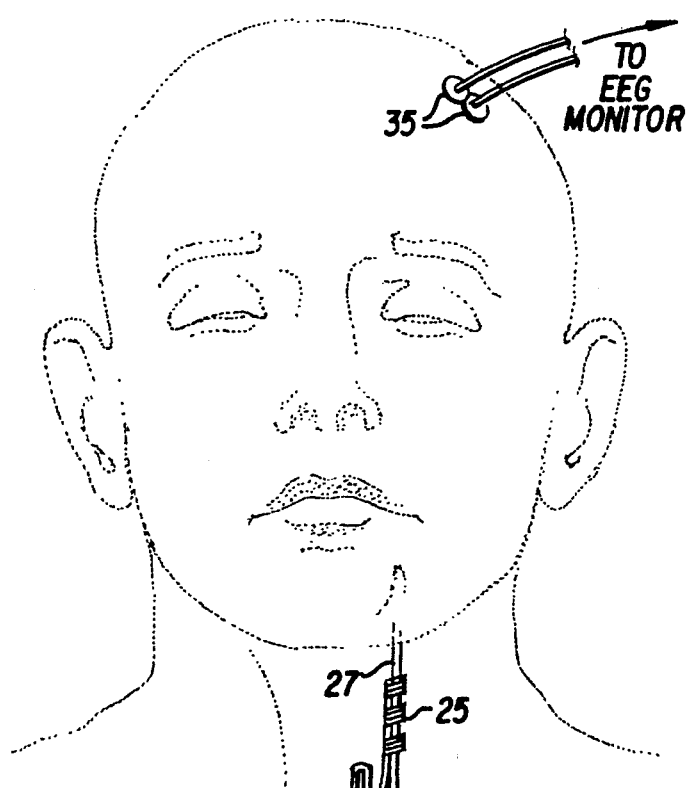
FIG. 3 is a simplified fragmentary illustration of a lead/ electrode system of a neurostimulator fully implanted in the patient's body for stimulating the vagus nerve, and with external electrodes for monitoring the patient's EEG.
Figure 3:
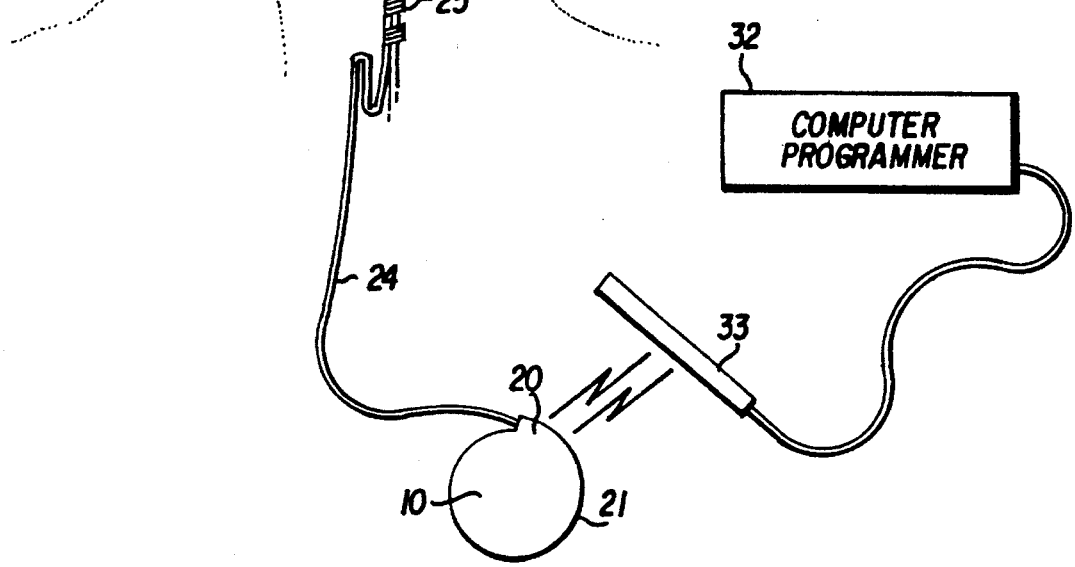

Alternatively, particularly where longer term treatment is prescribed, a lead/electrode assembly alone, or the entire neurostimulator, may be invasively implanted in the patient, as illustrated in FIG. 3. For that purpose, stimulus generator 10 is implemented in a hermetically sealed package of appropriately small size. The case 21 is composed of a material which is biologically compatible with the fluids and tissue of the patient's body, such as titanium, and the device is installed in a pocket formed by the surgeon just below the skin in the pectoral region. Further details of the distal end of the associated lead/electrode system 24, 25 are illustrated in FIG. 4. A stimulating electrode array 25 of lead 24 is implanted directly on the vagus nerve of the patient. The proximal end of the lead is electrically connected to the stimulus generator via standard connector and header 20 to apply the output signal of the stimulus generator directly to the vagus nerve. The generator and lead assembly form the overall neurostimulator. If only the electrode array and a portion of the lead are to be implanted, with electrical connection to an external stimulus generator, the proximal end of the lead is brought out for connection to the generator.

Implanted nerve electrode array 25 preferably comprises a bipolar stimulating electrode array of the type described in U.S. Pat. No. 4,573,481 issued Mar. 4, 1986. A surgical implantation site in the patient's neck is preferred for installation of the electrode array on vagus nerve 27. The two electrodes 25-1 and 25-2 of the array are wrapped about the nerve in the manner described in the '481 patent, and the assembly is secured to the nerve by a helical anchoring tether 28 described in U.S. Pat. No. 4,979,511 issued Dec. 25, 1990 and assigned to the same assignee as this application. To prevent the lead from shifting position on the nerve while still permitting it to flex with movements of the chest and neck, a suture connection 30 is made to nearby tissue.

The open helical design of the nerve electrode of the '481 patent renders it self-sizing and flexible, while minimizing mechanical trauma to the nerve and enabling body fluid interchange with the nerve. Each electrode conforms to the shape of the nerve, and its relatively large contact area with the nerve gives it a low threshold for stimulation. Structurally, the electrode array includes two ribbon electrodes of platinum which are individually bonded to the inside surface of each of helical loop electrodes 25-1, 25-2 of the array. Conductive lead wires are welded to respective ones of the conductive ribbon electrodes. Further details of the electrode array are described in the '481 patent.

By direct adjustment of knobs on an external generator, or by means of an external computer in the case of an implanted neurostimulator, in conjunction with section 15 of the generator, the physician can program the output pulse waveform of the generator for the desired modulation of electrical activity of the vagus nerve 27 when the stimuli are applied via the electrode. Timing signals for the logic and control functions of generator 10 are provided by a crystal oscillator 16, including provision of a clock where periodic or random stimulation is prescribed. A built-in antenna 17 enables communication between the stimulus generator, if implanted, and external computer programmer/monitor apparatus, for programming the desired electrical parameters of the pulse waveform, and for telemetry transmission of parameter values from the generator.

A conventional external personal computer (PC) 32 (FIG. 3) may be used together with programming software copyrighted by the assignee of the instant application with the Register of Copyrights, Library of Congress, or other suitable software. Once the system is programmed, it operates continuously at the programmed settings until they are reprogrammed by the attending physician. Communication between the external PC programmer and the implanted stimulus generator is achieved by conventional asynchronous serial telemetry transmission. A programming wand 33 may be used in the customary manner for implanted electronic medical devices.

Figure 5:
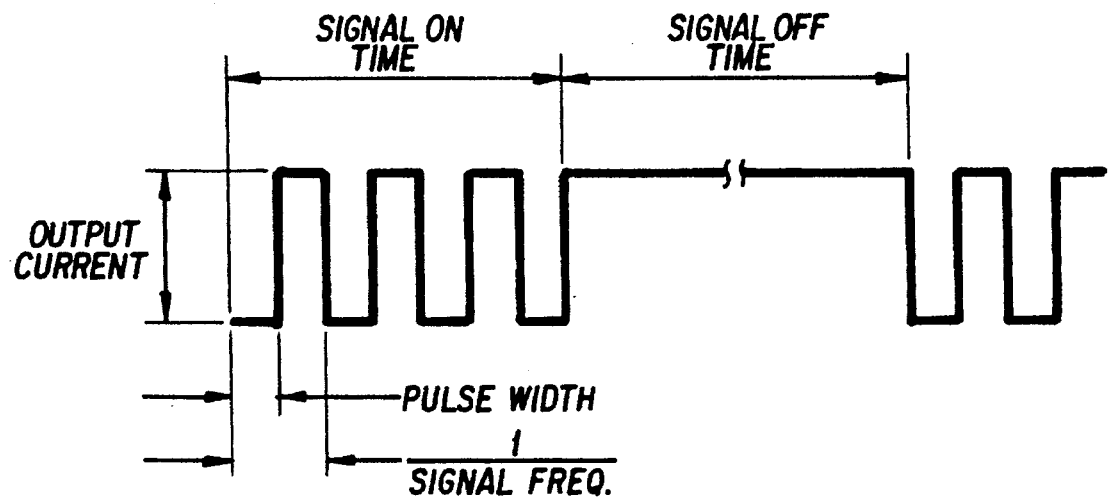
FIG. 5 is an illustrative idealized electrical output signal waveform of the stimulus generator for application to the nerve.

Referring to FIG. 5, an idealized pulse waveform is shown as the output signal from output section 19, for application to the unipolar electrode or bipolar electrode array. The electrical parameters of the pulse waveform include signal on-time, signal off-time, signal frequency, pulse width, and signal current or voltage, as shown in the Figure. The neurostimulator may be used to apply the programmed output pulse waveform to the electrode in a periodic manner or a continuous manner, with programming of electrical parameters as will be described presently.

The vagus nerve has approximately 100,000 fibers (axons) of different size, classified as A, B and C, which carry signals to and from the brain from and to other parts of the body. The myelinated A and B fibers are generally larger, faster conducting with lower stimulation thresholds, and have a particular strength-duration curve in response to a given stimulation pulse, compared to the unmyelinated C fibers. A and B fibers can be stimulated with relatively narrow pulse widths—from 50 to 200 microseconds (μs), for example—whereas C fibers typically require wider pulse widths (e.g., 300–1000 μs) and higher amplitudes for activation.

Electrical stimulation of nerve fibers results in neural signal flow in both directions, but each vagus nerve axon exhibits only unidirectional electrical conduction in normal circumstances. Somatic and visceral afferents (inward conducting nerve fibers that convey impulses toward a nerve center such as the brain or spinal cord) and efferents (outward conducting nerve fibers that convey impulses to an effector to stimulate it and produce activity) of the vagus nerve are generally of the C type, visceral afferents having cell bodies lying in masses or ganglia in the neck. The central projections terminate in the nucleus of the solitary tract which sends fibers to various regions of the brain, including the hypothalamus, thalamus, and amygdala. Others continue to the medial reticular formation of the medulla, the cerebellum, the nucleus cuneatus and other regions.

Electrical stimulation of vagal nerve afferent fibers in animals evokes detectable changes of the EEG in all of these regions, the nature and extent depending on the parameters of the stimulation. We postulate that synchronization of the EEG is produced when high frequency (>70 Hz) weak stimuli activate only the myelinated (A and B) nerve fibers, and that desynchronization of the EEG occurs when intensity of the stimulus is increased to a level that activates the unmyelinated (C) nerve fibers.

The presently preferred vagal stimulation strategy to bring a patient out of a coma, according to the invention, calls for modulating the vagus electrical activity to alesynchronize the EEG. In some instances, however, it may be desirable instead to synchronize the EEG. In the therapy regimen, the electrical parameters of the pulse waveform generated by the neurostimulator are selected (i.e., adjusted or programmed) to activate various fibers of the vagus nerve so as to modulate its electrical activity in a prescribed manner. The vagus nerve fibers can be selectively stimulated, such as A and not B and C; or A and B, but not C; or A, B and C, by the setting of pulse width, voltage (or current) and other parameters. C fibers conduct signals rather slowly, so they do not respond well to attempts at rapid stimulation. For example, if it were desired to increase desynchronous activity of the EEG by stimulating C fibers at 50 Hz, a short pulse train would be more effective than a long train. The fibers would become refractory to stimulation within a short period, rendering them incapable of tracking the pattern of a longer train. Short pulse trains may be repeated after suitable intervening recovery periods. Precise waveform pattern would be adjusted to the individual patient.

The amplitude and frequency of the applied pulse waveform may be selected to tune the appropriate nerve fibers for EEG desynchronization, preferably by vagal nerve stimulation at a frequency in the range from 20 to 75 Hertz (Hz) at a signal level above 0.1 volt. At frequencies above 75 Hz, the signal level should exceed 3 volts. The actual voltage required will depend on the type and geometry of the electrode and the impedance of the electrode-tissue interface.

To treat a comatose patient by desynchronizing EEG activity, the neurostimulator pulse waveform is programmed to a pulse frequency of 20 Hz, an output current of 1.5 milliamperes (mA), and a pulse width of 0.5 milliseconds (ms), for example. Table I, below, illustrates a suitable range of stimulation parameters for desynchronizing the patient's EEG activity, with the typical value of each parameter of the stimulating output signal for the treatment.

TABLE I

|  | Range | Typical |
|---|---|---|
| Pulse Width | 0.05–1.5 ms | 0.5 ms |
| Output Current | 0.1–5.0 mA | 1.5 mA |
| Frequency | 5–150 Hz | 20 Hz |
| ON Time | 5–5000 sec | 300 sec |
| OFF Time | 5–5000 sec | 20 sec |
| Frequency sweep | 10–100 Hz | Optional |
| Random frequency | 10–100 Hz | Optional |

Table II, below, illustrates a suitable range of stimulation parameters for synchronization of the patient's EEG activity, with typical values of the applicable parameters of the stimulating output signal for that purpose.

TABLE II

|  | Range | Typical |
|---|---|---|
| Pulse Width | 0.05–1.5 ms | 0.1 ms |
| Output Current | 0.1–5.0 mA | 1.0 mA |
| Frequency | 5–150 Hz | 90 Hz |
| ON Time | 5–5000 sec | 30 sec |
| OFF Time | 5–5000 sec | 30 sec |
| Frequency sweep | 10–100 Hz | Optional |
| Random frequency | 10–100 Hz | Optional |

Preferably, the prescribed pulse waveform pattern is applied continuously to the vagus nerve, but alternatively, periodic or random application may be employed.

If the comatose patient exhibits a synchronized EEG, as normally would be expected, an appropriate predetermined set of desynchronizing electrical parameters of the output pulse waveform of the neurostimulator may be automatically selected by the device's microprocessor. That signal is then applied to the vagus nerve for a predetermined period of time. The EEG should be monitored and if it remains synchronized, the desynchronizing signal is applied to the vagus nerve for another predetermined time interval. If, however, the EEG of the comatose patient, on examination, initially exhibits a alesynchronized EEG pattern, the stimulation signal is selected to have a synchronizing effect, and that signal is then applied to the vagus nerve.

Figure 6:
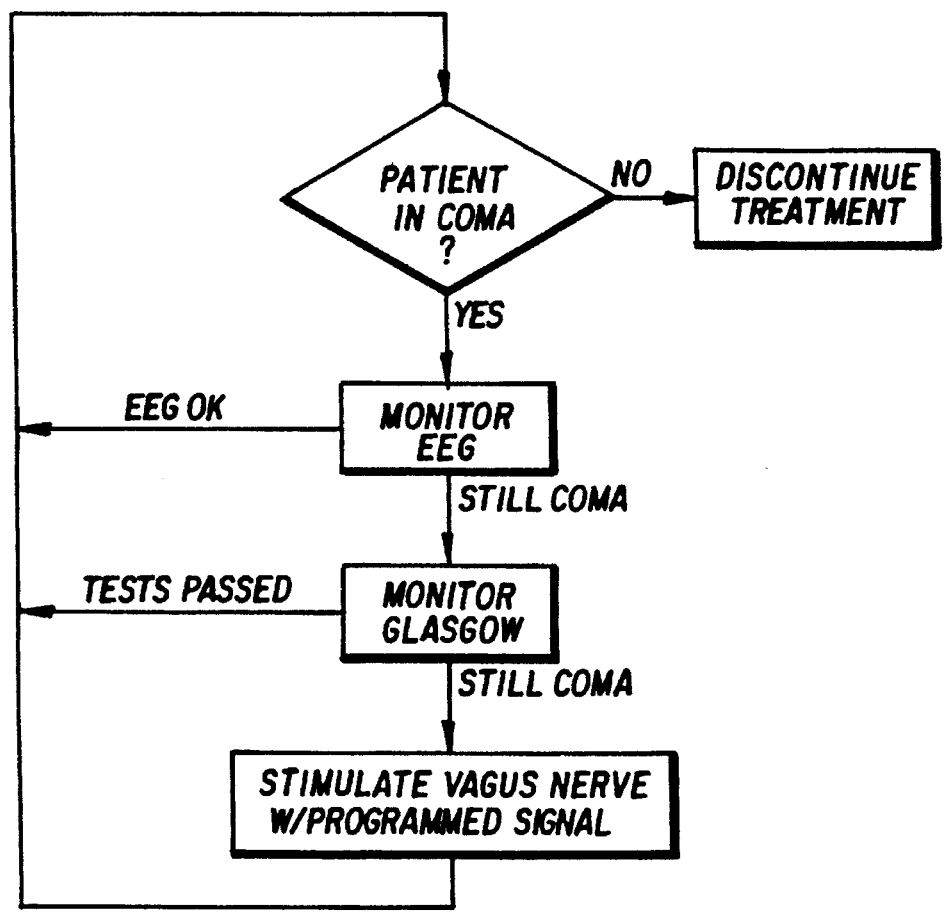
FIG. 6 is a flow chart to illustrate a method of treating the comatose patient according to the invention.

The patient's EEG is monitored in the usual manner, with appropriately positioned electrodes, such as 35 in FIG. 3. Additionally, the physician may monitor the progress of the patient by resort to factors employed in the Glasgow coma scale, including motor response, verbal response, and eye opening response to designated stimuli. A flow diagram illustrating a method of treatment employing EEG and Glasgow monitoring before and after stimulation is presented in FIG. 6.

Although a preferred embodiment and method of treating patient coma have been described herein, it will be apparent to those skilled in the art from the foregoing description that variations and modifications may be made without departing from the true spirit and scope of the invention. For example, a substantially external stimulus generator may even be simplified by use of an RF power device of appropriate energy level, with the only implanted components being the lead/electrode assembly and/or an associated coil and DC rectifier. The programmed pulse waveform is transmitted through the skin via an RF carrier, and then rectified to regenerate a pulsed signal for application to the vagus nerve.

Accordingly, it is intended that the invention shall be limited only to the extent required by the appended claims and the rules and principles of applicable law.

What is claimed is:

1. A method of treating a patient in coma, comprising the steps placing at least one electrode of an electrode array in juxtaposition with a preselected cranial nerve of the patient for electrical stimulation thereof;

applying an electrical pulse waveform to said electrode array to stimulate said cranial nerve; and adjusting electrical parameters of said pulse waveform to modulate electrical activity of said cranial nerve in an effort to rouse the patient from the coma.

2. The method of claim 1, further including monitoring the response of the patient to the treatment according to Glasgow coma scale, to determine degree of conscious impairment of the patient.

3. The method of claim 1, wherein the step of placing said at least one electrode comprises placing said electrode array as a bipolar electrode array in juxtaposition with the patient's vagus nerve.

4. The method of claim 3, further including monitoring the response of the patient to the treatment according to Glasgow coma scale, to determine degree of conscious impairment of the patient.

5. The method of claim 1, wherein the step of placing said at least one electrode comprises positioning an electrode in the patient's throat for stimulating a region of the vagus nerve in the patient's neck.

6. The method of claim 1, wherein the step of placing said at least one electrode comprises implanting said electrode array as a bipolar nerve electrode array on the vagus nerve in the neck of the patient.

7. The method of claim 6, wherein the step of adjusting includes programming electrical parameters of said pulse waveform comprising at least some of the parameters of pulse frequency, pulse width, pulse current, pulse voltage, waveform on time, and waveform off time.

8. The method of claim 7, wherein the step of applying said pulse waveform to the electrode array comprises periodically applying the pulse waveform with programmed electrical parameters to the patient's vagus nerve.

9. The method of claim 7, wherein the step of applying said pulse waveform to the electrode array comprises continuously applying the pulse waveform with programmed electrical parameters to the patient's vagus nerve.

10. The method of claim 7, wherein the step of programming electrical parameters of said pulse waveform comprises programming said electrical parameters of the pulse waveform to modulate electrical activity of the patient's vagus nerve when the pulse waveform is applied to the electrode array thereon so as to exercise control over the patient's EEG activity.

11. The method of claim 10, wherein the step of programming electrical parameters of said pulse waveform comprises programming said electrical parameters of the pulse waveform to modulate electrical activity of the patient's vagus nerve when the pulse waveform is applied to the electrode array thereon so as to desynchronize the patient's EEG activity.

12. The method of claim 10, wherein the step of programming electrical parameters of said pulse waveform comprises programming said electrical parameters of the pulse waveform to modulate electrical activity of the patient's vagus nerve when the pulse waveform is applied to the electrode array thereon so as to synchronize the patient's EEG activity.

13. The method of claim 10, further including monitoring the patient's EEG activity to determine whether said EEG activity is synchronized or desynchronized, and wherein the step of programming electrical parameters of said pulse waveform comprises programming said electrical parameters of the pulse waveform to modulate electrical activity of the patient's vagus nerve when the pulse waveform is applied to the electrode array thereon so as to reverse the synchronicity or desynchronicity of the patient's EEG activity as determined by said monitoring.

14. The method of claim 13, further including monitoring the response of the patient to the treatment according to Glasgow coma scale, to determine degree of conscious impairment of the patient.

15. A method of therapy for a comatose patient, comprising the steps of:

placing an electrode array on said patient to electrically interact with a preselected cranial nerve of the patient;

applying an electrical pulse waveform to said electrode array to stimulate said preselected cranial nerve; and programming electrical parameters of said applied pulse waveform to modulate electrical activity of said cranial nerve in an effort to rouse the patient from the coma.

16. The method of claim 15, further including monitoring the response of the patient to the therapy according to Glasgow coma scale, to determine degree of conscious impairment of the patient.

17. The method of claim 15, wherein the step of placing said electrode array comprises placement thereof to electrically interact with the patient's vagus nerve, so that upon applying said waveform to the electrode array, the electrical interaction therebetween will stimulate the patient's vagus nerve.

18. The method of claim 17, wherein the step of programming electrical parameters of said pulse waveform comprises programming at least some of the parameters of pulse frequency, pulse width, pulse current, pulse voltage, waveform on time, and waveform off time of said applied pulse waveform.

19. The method of claim 18, wherein the step of programming electrical parameters of said pulse waveform comprises programming said electrical parameters of the pulse waveform to modulate electrical activity of the patient's vagus nerve when the pulse waveform is applied to the electrode array on the patient so as to exercise control over the patient's EEG activity.

* * * * *